United States Patent [19]
Devreux

[11] 4,343,231
[45] Aug. 10, 1982

[54] BREWING APPARATUS HAVING SAMPLING MEANS DELIVERING SUSPENSION TO FERMENTING VESSEL

[75] Inventor: André F. Devreux, Mons, Belgium

[73] Assignee: Compagnie Internationale de Participation et d'Investissement "Cipari" S.A., Luxembourg, Luxembourg

[21] Appl. No.: 227,555

[22] Filed: Jan. 22, 1981

[30] Foreign Application Priority Data

Feb. 7, 1980 [LU] Luxembourg .......................... 82145

[51] Int. Cl.³ .......................... C12G 3/04; C12G 3/02
[52] U.S. Cl. .................................... 99/277.2; 426/11; 435/291
[58] Field of Search .................. 99/276, 277, 277.1, 99/277.2, 278, 323.1, 323.2; 435/4, 291, 287; 426/11

[56] References Cited

U.S. PATENT DOCUMENTS

| | | | |
|---|---|---|---|
| 3,871,272 | 3/1975 | Melandri | 99/276 |
| 3,875,303 | 4/1975 | Betriebs | 99/276 |
| 3,959,120 | 5/1976 | Pollock | 99/276 |
| 4,264,740 | 4/1981 | Christ | 435/291 |
| 4,265,544 | 5/1981 | Banno et al. | 435/291 |

Primary Examiner—Robert W. Jenkins
Attorney, Agent, or Firm—Sughrue, Mion, Zinn, Macpeak and Seas

[57] ABSTRACT

A process for adjusting the amount of yeast introduced into a fermentative liquid comprises periodically taking a sample from a mass of suspended yeast maintained in movement in a closed circuit, subjecting the sample to fermentation by adding a nutrient element, and adjusting the supply of yeast to the liquid in accordance with the fermentative power of the treated yeast sample. The implementing plant comprises a container having a conical bottom containing yeast suspended in a liquid, a pipe connecting the bottom of the container to a fermentation tank, and a regulating or adjusting pump for supplying yeast from the container into the tank. A pipe for recycling the suspended yeast in the container is provided, as well as means for ensuring, during a predetermined time interval, the recycling of the suspension of yeast from the bottom of the container to the upper part thereof. Sampling means periodically extract a predetermined volume of the recycling yeast suspension and deliver it to a small fermenting vessel whereat the nutrient agent is supplied. Means are then provided for determining the fermentative power of the yeast sample and for adjusting the yeast supply of the fermentation tank in accordance therewith.

9 Claims, 3 Drawing Figures

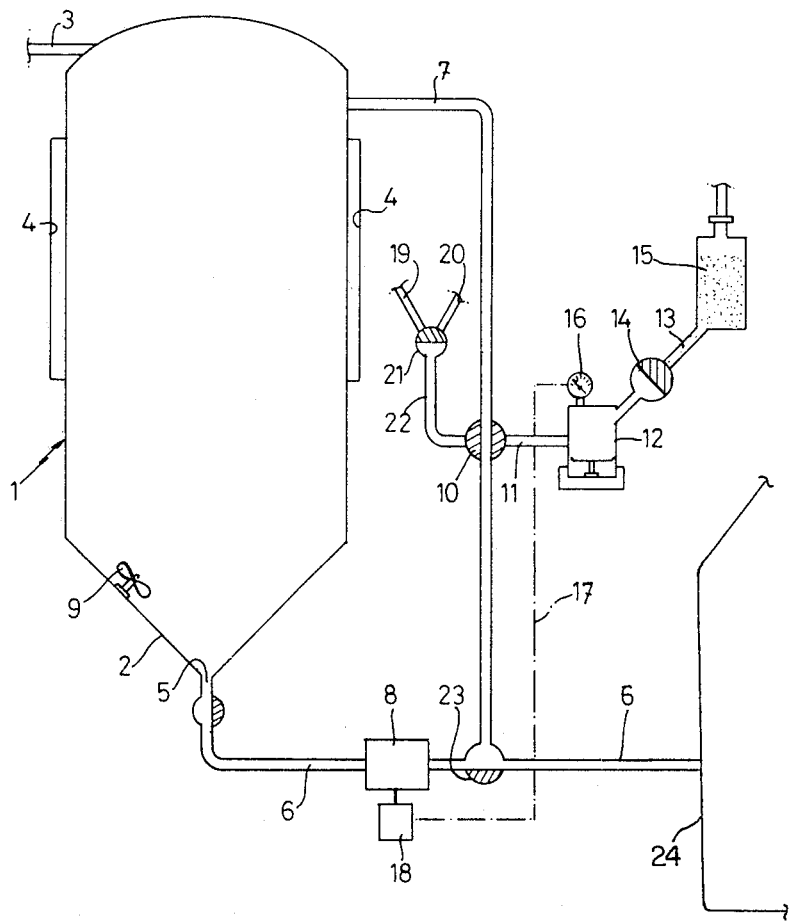

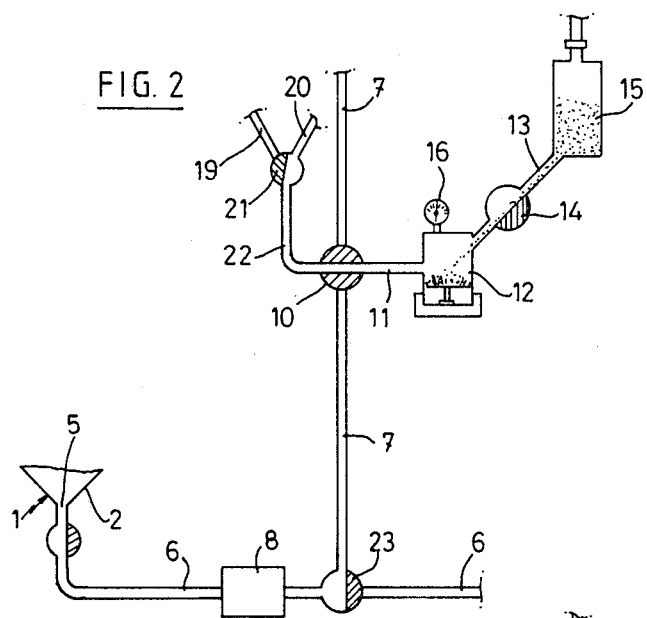
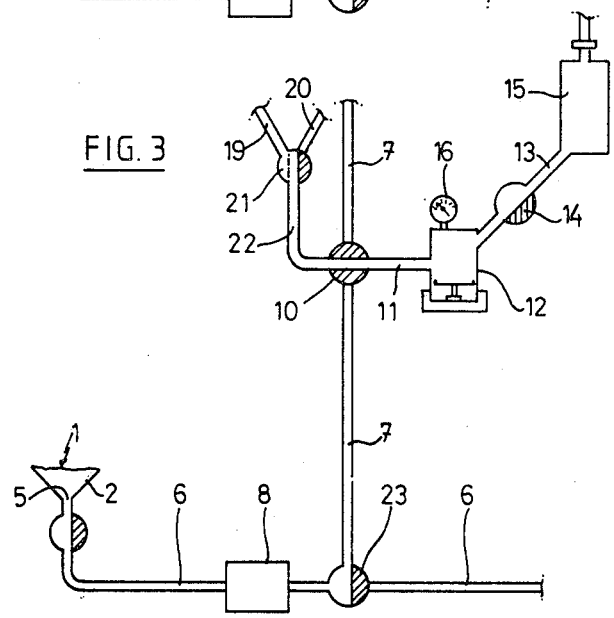

BREWING APPARATUS HAVING SAMPLING MEANS DELIVERING SUSPENSION TO FERMENTING VESSEL

BACKGROUND OF THE INVENTION

This invention relates to improvements to the process and plants using yeasts for the manufacture of beverages, such as beer, cider, wine and other alcoholized beverages, as well as of bakery products.

In the brewery field, it is known to stock an aqueous suspension of yeast or leaven resulting from a yeast culture produced in a propagator and/or from the harvesting of yeast previously used in the manufacture of wort, in a stocking container, from which a determined amount of yeast suspension is tapped and sent through means, such as a regulating pump, into a wort fermentation tank. The regulating pump is inserted in a pipe connecting the stocking container to the fermentation tank.

On the other hand, it is known that the quality of the yeast suspension contained in the stocking container is variable, so that the amount of said suspension to be introduced into the fermentation tank is also variable, in accordance with various factors, such as the compacity of the yeast, the fermentative power thereof and the like.

Various methods are known for adjusting the volume and the weight of the yeast suspension to be used in a fermentation tank having a given capacity. In one known method, a sample of yeast is taken from the stocking container and the compacity of said yeast is measured by centrifugation in a laboratory. According to another known method, a minimum amount of suspended yeast is injected into a fermentation tank and after said amount of yeast is uniformly distributed in the wort contained in the fermentation tank, a sample of yeast-containing fermented wort is taken and the number of yeast cells present in said sample is counted. Taking the results of this counting into account, an additional amount of yeast is introduced into the fermentation tank so as to ensure an optimum fermentation of the wort in said tank.

These known methods have several drawbacks. A common drawback of both methods is that they do not allow a qualitatively uniform fermentation of the wort. Moreover, the first known method, disclosed in the preceding paragraph, is time consuming, the sampling and the measurement of the compacity of the yeast suspension in a laboratory needing a lot of time, so that it is practically not possible to determine, within the prescribed time, the fermentative power of the used yeast. The second known process which involves a cell counting is not precise, since it does not take into account the dead cells as well as the cells, the fermentative power of which has been detrimentally effected.

This invention relates to a process and to a plant avoiding the drawbacks of the known methods.

BRIEF DESCRIPTION OF THE INVENTION

The invention relates first to a process for adjusting the amount of yeast to be introduced into a fermentation enclosure containing a fermentative liquid.

The process according to this invention essentially comprises the steps of taking, at predetermined time intervals, a sample of a given volume from a mass of suspended yeast while said mass is maintained in movement in a closed circuit, submitting said sample to a fermentation by adding thereto a nutrient element and adjusting the supply of yeast to the fermentation enclosure in accordance with the fermentative power of the treated yeast sample.

In accordance with a feature of the process according to the invention, the yeast supply of the fermentative enclosure is adjusted, for example, in respect of the maximum pressure increase caused by the fermentation of the yeast sample, this sample being preferably taken downstream the means, such as the regulating pump, to be used for supplying the fermentation enclosure containing the fermentative liquid.

This invention relates to a plant for adjusting the amount of yeast to be introduced into a fermentation enclosure, comprising a container having a conical bottom containing yeast suspended in a liquid and a pipe connecting the bottom of said container to at least one fermentation tank, as well as means, such as a regulating or adjusting pump, for supplying yeast from the yeast container into the fermentation tank.

According to this invention, the plant mainly comprises a pipe for recycling the suspended yeast contained in said container, as well as means for ensuring, during a predetermined time interval, the recycling of the suspension of yeast from the bottom of said container to the upper part of this container, means for taking from said recycling pipe, at selected moments, a sample having a predetermined volume of the yeast suspension, while the latter is recycled and for sending said sample into a little fermenting vessel to which a nutrient agent is supplied, means for determining the fermentative power of the yeast sample in the fermenting vessel and means for adjusting the yeast supply of the fermentation tank in accordance with the fermentative power of the yeast sample, as determined in the fermenting vessel.

In accordance with a feature of the plant according to this invention, a regulating pump for supplying yeast to the fermentation tank is mounted in the pipe connecting the bottom of the yeast container to the fermentation tank, upstream the pipe recycling the yeast suspension into the yeast container. The means for taking yeast samples preferably consist of a valve which, in one position, sends or allows a predetermined amount of yeast suspension to be sent into the fermenting vessel. According to the invention, said valve may be a valve having more than two ways, which, in a first position, allows the recycling of the suspended yeast into the yeast container, which, in a second position, allows the sampling of yeast and the sending of the yeast sample into the fermenting vessel and which, in a third position, connects a cleaning liquid source to the fermenting vessel or a compressed air source to this fermenting vessel.

The plant according to this invention preferably also contains means for adjusting the duration of the operation of said regulating pump, in accordance with the fermentative power of the yeast sample, as determined in the fermenting vessel.

DETAILED DESCRIPTION OF THE INVENTION

Other features and details of the invention will appear from the following detailed description of the attached drawings which show schematically and only for illustrative purposes, an embodiment of a plant according to this invention. In said drawings:

FIG. 1 is a vertical section of a plant according to this invention;

FIG. 2 is a section of a part of the plant showing how yeast samples are taken from the circuit of recycling the yeast contained in the container in which said yeast is stocked, and FIG. 3 is a vertical section similar to that of FIG. 2 showing how the cleaning of the plant is effected.

In the various figures, the same reference numbers refer to identical elements.

FIG. 1 shows a container 1 for stocking a suspension of yeast in a liquid, such as brewery wort. This container is preferably a cylindrical container having a conical bottom 2. A suspension of yeast coming from a device for culturing fresh yeast and/or from a tank for the fermentation of beer wort (not shown) is collected through an inlet 3 in said container 1. The yeast stocking container 1 is surrounded by a cooling jacket 4, in which a cooling agent flows, so as to maintain the yeast suspension at a temperature of about 0° C. in the container 1.

To the lower end 5 of the yeast stocking container 1 is connected a supply pipe 6 for carrying the yeast suspension from the container 1 to a tank 24 (shown schematically) used for the fermentation of beer wort.

To the supply pipe 6 is connected a recycling pipe 7 which ends at the upper part of the container 1. This recycling pipe 7 is preferably positioned downstream means, such as an adjusting or regulating pump 8, which is used for carrying the yeast suspension from the container 1 toward the fermentation tank. However, the recycling pipe 7 may be connected to the supply pipe 6 upstream the regulating pump 8; in this latter case, a particular recycling pump must be provided in the circuit for the recycling of the yeast suspension, said circuit comprising the recycling pipe 7 and the container 1 which is provided, preferably near its conical bottom, with a stirrer 9, for example of the electro-magnetic known type.

In the recycling pipe 7 is mounted a four-way valve 10 which, in the position shown in FIG. 1, allows a continuous recycling of yeast suspension from the lower end of the container 1 to its upper end. Due to the stirrer 9 and to the recycling pipe 7, it is possible to maintain a homogeneous composition of the yeast suspension in the container 1, so that when it is desired to take a sample of yeast, as described hereinafter, this sample is homogeneous and represents really the mean quality of the yeast suspension stocked in the container 1.

To valve 10 is connected a sampling pipe 11 which ends in a fermenting vessel 12, in which a sample of suspended yeast having a predetermined weight or volume is collected, when the valve 10 has been moved into the position shown in FIG. 2.

To the sample collected in the fermenting vessel 12 is added a nutrient liquid supplied, through a pipe 13 equipped with a cock 14, from a receptacle 15 containing a supply of a nutrient liquid, such as an aqueous solution of sugar. The amount of nutrient liquid added to the yeast sample collected in the fermenting vessel 12 is adjusted by the duration of opening or by the degree of opening of the cock 14.

In the fermenting vessel 12, the yeast sample is heated by a suitable heating device to a proper temperature for causing a fermentation or growth of the yeast with release of carbon dioxide. To the fermenting vessel 12 is associated a device 16 which may be a device for detecting pressure, pH or other modifications or phenomena, which show the fermentative power of the yeast sample and controls, as indicated by the dotted line 17, a motor 18 operating the regulating pump 8, so that the duration of operation of this pump or the output thereof and therefore the amount of suspended yeast sent from the container 1, through the supply pipe 6, to the fermentation tank are adjusted in accordance with the quality of the yeast container in the container 1. The fermentative power of said yeast may be measured at any time, by admitting a sample thereof into the fermenting vessel 12, in which the quality of the yeast may be tested within a few minutes.

When the operation of the plant is stopped, said plant may be cleaned by maintaining the valve 10 in the position illustrated in FIG. 2 and by allowing first the admission of a cleaning liquid, such as a caustic soda solution from a container (not shown) through a pipe 19, and thereafter the admission of compressed air through a pipe 20, the pipes 19 and 20 being connected to a three-way valve 21 connected to a pipe 22 which is itself connected to said valve 10.

A valve 23 or a similar device may be used for putting the plant in a working or non working condition.

The sampling of yeast may take place, according to this invention, during the supply of yeast to the fermentation tank by the regulating pump; in this case, the device for measuring the fermentative power associated to the fermenting vessel 12 controls the stop of the regulating pump or its output, in such a manner that a suitable amount of yeast is sent into the fermentation tank, in accordance with the quality of the yeast.

It is pointed out that the invention is not limited to the above described details and that these details may be modified within the scope of the invention.

Thus, although the process and the plant according to the invention have been described hereabove when applied in a brewery, the art worker will easily be able to adapt said process and said plant to the fields of manufacture of cider, wine and other alcoholized beverages. The process according to this invention may generally be used in all industrial fields where yeast is used, namely in the bakery field.

I claim:

1. Plant for adjusting the amount of yeast to be introduced into a fermentation enclosure, comprising a container having a conical bottom containing yeast suspended in a liquid and a pipe connecting the bottom of said container to at least one fermentation tank, as well as a regulating pump, for supplying yeast from the yeast container into said fermentation tank, a pipe for recycling the suspended yeast contained in said container, means for insuring, during a predetermined time interval, the recycling of the suspension of yeast from the bottom of said container to the upper part of this container, means for taking from said recycling pipe, at selected moments, a sample having a predetermined volume of the yeast suspension, during the recycling thereof, and for sending said sample into a little fermenting vessel to which a nutrient agent is supplied, means for determining the fermentative power of the yeast sample in the fermenting vessel and means for adjusting the yeast supply of the fermentation tank in accordance with the fermentative power of the yeast sample as determined in the fermenting vessel.

2. Plant in accordance with claim 1, wherein a regulating pump for supplying yeast to the fermentation tank is mounted on the pipe connecting the bottom of the yeast container to the fermentation tank upstream the pipe recycling the yeast suspension into said yeast container.

3. Plant in accordance with claim 2, comprising means for adjusting the duration of the operation of said regulating pump, in accordance with the fermentative power of the yeast sample, as determined in the fermenting vessel.

4. Plant in accordance with claim 1, wherein said fermenting vessel is provided with a device determining a modification of phenomenon occuring in the fermenting vessel, the operation of the regulating pump being adjusted by said device.

5. Plant in accordance with claim 1, wherein a receptacle containing a nutrient liquid is connected by a pipe to said fermenting vessel, a valve allowing to regulate the amount of nutrient liquid introduced into the fermentation vessel in accordance of the amount of yeast sample taken and sent into the fermentation vessel.

6. Plant in accordance with claim 1, wherein the recycling pipe is provided with a valve allowing to interrupt the flow of suspended yeast in said recycling pipe.

7. Plant in accordance with claim 1, wherein said yeast container has a mixer.

8. Plant in accordance with claim 1, wherein the means for taking a sample consist of a valve which, in one position, sends or allows a predetermined amount of yeast suspension to be sent into the fermentation vessel.

9. Plant in accordance with claim 8, wherein said valve is a valve having more than two ways, which, in a first position, allows the recycling of the suspended yeast into the yeast container, which, in a second position, allows the sampling of yeast and the sending of the yeast sample into the fermenting vessel, and which, in a third position, connects a cleaning liquid source to the fermenting vessel or a compressed air source to this fermenting vessel.

* * * * *